(12) United States Patent
Cantor

(10) Patent No.: US 6,852,525 B1
(45) Date of Patent: Feb. 8, 2005

(54) MAMMALIAN CELL CULTURE CHAMBER

(75) Inventor: Hal C. Cantor, Farmington Hills, MI (US)

(73) Assignee: Advanced Sensor Technologies, Farmington Hills, MI (US)

( * ) Notice: Subject to any disclaimer, the term of this patent is extended or adjusted under 35 U.S.C. 154(b) by 0 days.

(21) Appl. No.: 10/129,248

(22) PCT Filed: Nov. 2, 2002

(86) PCT No.: PCT/US00/41800

§ 371 (c)(1), (2), (4) Date: Sep. 6, 2002

(87) PCT Pub. No.: WO01/48144

PCT Pub. Date: Jul. 5, 2001

Related U.S. Application Data

(60) Provisional application No. 60/163,470, filed on Nov. 2, 1999.

(51) Int. Cl.$^7$ ................................................. C12M 1/34
(52) U.S. Cl. ............................... 435/288.3; 435/288.7; 435/289.1; 204/403.1; 324/682
(58) Field of Search .......................... 435/288.3, 287.1, 435/288.7, 289.1; 204/403.1; 324/447, 692; 356/36, 246

(56) References Cited

U.S. PATENT DOCUMENTS

| | | | |
|---|---|---|---|
| 4,054,646 A | 10/1977 | Giaever | 424/12 |
| 4,920,047 A | 4/1990 | Giaever et al. | 435/7 |
| 5,187,096 A | 2/1993 | Giaever et al. | 435/291 |
| 5,563,067 A | 10/1996 | Sugihara et al. | 435/287.1 |
| 5,759,846 A * | 6/1998 | Stoppini et al. | 435/284.1 |
| 5,810,725 A | 9/1998 | Sugihara et al. | 600/372 |
| 5,981,268 A | 11/1999 | Kovacs et al. | 435/287.1 |
| 6,130,056 A | 10/2000 | Correges | 435/29 |
| 6,132,683 A | 10/2000 | Sugihara et al. | |

OTHER PUBLICATIONS

Brazell, M.P., Feng, J., Kasser, R.J., Renner, K.J., Adams, R.N. "An improved method for Nation coating carbon fiber electrodes for in vivo electrochemistry." J. Neurosci. Meth., 22:167–172, 1987.

Campanella, L., Colapicchioni, G., Favero, G., Sammartino, M.P., Tomassetti, M. "Organophosphorus pesticide (Paraoxon) analysis using solid state sensors." Sensors and Actuators B 33 (1996 25–33).

Cho, Y.A., Lee, H.S., Cha, G.S., Lee, Y.T. "Fabrication of butyrylcholinesterase sensor using polyurethane–based ion–selective membranes." Biosens Biolectron Apr. 30, 1999; 14(4):435–9.

Ghosh, P.M. et al., "Monitoring Electropermeabilization in the Plasma Membrane of Adherent Mammalian Cells." Biophys. Journal, 64, 1602–09 (1993).

Giaever, I. et al., "Use of Electric Fields to Monitor the Dynamical Aspect of Cell Behavior in Tissue Culture." IEEE Transactions on Biomedical Engineering, vol. BME–33, No. 2, Feb. 1986.

Keese, C.R. et al., "A Whole Cell Biosensor Based on Cell–Substrate Interactions." Annual International Conference of the IEEE Engineering in Medicine and Biology Society, vol. 12, No. 2, (1990).

Keese, C.R., et al, "A Biosensor that Monitors Cell Morphology with Electrical Fields." IEEE Engineering in Medicine and Biology, Jun./Jul. 1994, 402–08.

Kowolenko, M. et al., "Measurement of Macroophage Adherence and Spreading with Weak Electric Fields." Journal of Immunological Methods, 127, 71–77 (1990).

Lind et al., "Single cell Mobility and Adhesion Monitoring Using Extracellular Electrodes." Biosensors and Bioelectronics, 6, 359–67 (1991).

Mulchandani, P., Mulchandani. A., Kaneva, I., Chen, W. "Biosensor for direct determination of organophosphate nerve agents. 1. Potentiometric enzyme electrode." Biosens Bioelectron Jan. 1, 1999; 14(1):77–85.

Russell, R.J., Pishko, M.V., Simonian, A.L., Wild, J.R. "Poly(ethylene glycol) hyrogel–encapsulated fluorophore–enzyme conjugates for direct detection of organophosphorus neurotoxins." Analytical Chemistry Nov. 1, 1999;71(21):4909–12.

* cited by examiner

Primary Examiner—David A. Redding
(74) Attorney, Agent, or Firm—Kenneth I. Kohn

(57) ABSTRACT

The present invention relates to a cell culture chamber (10) having a sterile environment (12) for the culture of cells, a cover (14) for allowing for a transfer of pits and a sensor array.

5 Claims, 9 Drawing Sheets

MAMMALIAN CELL CULTURE CHAMBER

REFERENCE TO RELATED APPLICATIONS

This patent application is a National Phase Concerning a Filing Under 35 U.S.C 371, claiming the benefit of priority of PCT/US00141800, filed Nov. 2, 2000, which claims the benefit of priority of U.S. Provisional Ser. No. 60/163,470, filed Nov. 2, 1999, all of which are incorporated herein by reference.

CROSS REFERENCE TO RELATED APPLICATIONS

This application claims the benefit of priority under 35 U.S.C. Section 119(e) of United States Patent Application Number 60/163,470, filed Nov. 2, 1999, which is incorporated herein by reference.

GRANT INFORMATION

This invention as made with government support under grant number 1 R43NS37989-01 awarded by the National Institute of Health (NIH). The government has certain rights to the invention.

BACKGROUND OF THE INVENTION

1. Technical Field

The present invention relates to a cell culture chamber 10. More specifically, the present invention relates to a cell culture chamber 10 utilizing a sensor array.

2. Background Art

Biosensors sensors including biological materials employed to detect and/or monitor an environment, offer several advantages. Biosensor development can utilize the highly sensitive nature of biological materials to directly detect the presence or absence of analytes by their effect upon cellular metabolism. For example, utilizing cultured cell systems it is possible to screen for a broad range of toxins, thereby achieving a fast turn-around time, while maintaining high sensitivity. Moreover, a degree of selectively can be achieved by a choice of cell type.

Cellular metabolism refers to the orchestration of the chemical and enzymatic reactions that constitute the life process of a cell. These reactions include a vast number of different chemical and enzymatic reactions, relating to the growth and maintenance of the cell. These chemical and enzymatic reactions occur simultaneously within an active cell. Moreover, these reactions do not take place in isolation; rather the pace of each reaction is regulated, in turn, by the product of one or more other reactions. Overall, the organization of cellular metabolism is embedded in a vast network of inter-related cellular reactions. Given this interdependency, it is apparent that analytes that affect one or more aspects of cellular metabolism are likely to manifest their impact on characteristics of the cell, including impedance, action potential parameters, including action potential rate, action potential amplitude, and action potential shape, among others; membrane conductance, membrane capacitance and secretion of cellular products such as hormones, neurotransmitters, and other cellular metabolites.

Because of the above advantages, biosensors including live, intact cells (referred to as hybrid biosensors) have several commercially significant applications. For example, such biosensors are particularly useful in detecting chemical and biological warfare (CBW) agents. Biosensors may also supplement existing methods for pharmaceutical screening. It is possible that this type of biosensor technology will eliminate, or at least greatly reduce, animal testing employed in pharmaceutical screening.

Some progress in the development of hybrid biosensor technology has been described within the scientific literature. For example, techniques have been described by Giaever and Keese (in conjunction with others) to monitor the impedance characteristics at celuelectrode interfaces. See Kowolenko M., et al., 1990; Keese C. R., et al., 1990; Ghosh, P. M., et al., 1993; Keese, C. R., et al., 1994; Giaever, I., et al., 1986; U.S. Pat. Nos. 4,054,646; 4,920,047; and 5,187,096. However, the systems described by Giaever and Keese utilize large area electrodes (e.g., 250 $\mu$m diameter) which cannot be completely covered by a single cell. Therefore, accurate measurement of an individual cell's impedance characteristics or secretory profiles, is interfered with by the parallel impedance or secretory profiles of the uncovered electrode area and the impedance or secretory profiles of cellcell contact areas (due to the space between adjacent cells). Moreover, the efforts of Giaever and Keese reveal only motility changes in cells. Further, cellular membranes are modeled as having a constant capacitance and conductance; any changes in capacitance and conductance are explained in terms of varying cellular membrane area.

In Lind et al., 1991, a system using relatively large area electrodes similar to that described above was employed, as well as a system utilizing electrodes smaller than the cell to be monitored. In this system, single cell effects could be examined without the shunting effects described above, but this system was only used to monitor cell motility by means of changes in the impedance. Moreover, in such systems membrane conductance and capacitance was presumed to be constant. Accordingly, there remains a need for a technique that utilizes electrodes smaller than a cell's diameter, but which provides for monitoring changes in cellular membrane capacitance and conductance, as well as being capable of monitoring secreted cellular products such as hormones, neurotransmitters and cellular metabolites. Such a technique would also permit monitoring of activation of voltagegated ionic channel conductance. In addition, such a technique would permit detection and monitoring of compounds that affect the impedance, action potential parameters, membrane conductance, membrane capacitance of a cell, and cell/substrate seal resistance, as well as being capable of monitoring secreted cellular products such as hormones, neurotransmitters and cellular metabolites.

For example, voltage-gated $Na^+$ channels (among other ion channels) help make nerve cells electrically excitable and enable them to conduct action potentials. When the membrane of a cell with many $Na^+$ channels is partially depolarized by a momentary stimulus, some of the channels promptly open, allowing $Na^+$ ions to enter the cell. The influx of positive charge depolarizes the membrane further, thereby opening more channels, which admit more $Na^+$, causing still further depolarization. This process continues in a self-amplifying fashion until the membrane potential has shifted from its resting value of about −70 mV all the way to the $Na^+$ equilibrium potential of about +50 mV. At that point, where the net electrochemical driving force for the flow of $Na^+$ is zero, the cell would come to a new resting state with all its $Na^+$ channels permanently open, if the open channel conformation were stable. The cell is saved from such a permanent electrical tetanus by the automatic inactivation of the $Na^+$ channels, which now gradually close and stay closed until the membrane potential has returned to its initial negative resting value. The whole cycle, from initial stimulus to return to the original resting state, takes a few milliseconds or less.

In many types of neurons, though not all, the recovery is hastened by the presence of voltagegated $K^+$ channels in the plasma membrane. Like the $Na^+$ channels, these channels open in response to membrane depolarization, but they do so relatively slowly. By increasing the permeability of the membrane to $K^+$ just as the $Na^+$ channels are closing through inactivation, the $K^+$ channels help to bring the membrane rapidly back toward the $K^+$ equilibrium potential, so returning it to the resting state. The repolarization of the membrane causes the $K^+$ channels to close again and allows the $Na^+$ channels to recover from their inactivation. In this way the cell membrane can be made ready in less than a millisecond to respond to a second depolarizing stimulus.

Examining the membrane potential relative to time, an action potential exhibits various characteristics or parameters, including action potential rate (if cells spontaneously depolarize), action potential amplitude, and action potential shape, among others. Action potential rate refers to the frequency with which a cell produces an action potential (rapid depolarization). Action potential amplitude refers to the height of the peak depolarization that occurs in the course of the action potential. Action potential shape refers to the time course of the depolarization and repolarization.

It would therefore be useful to develop a cell chamber 10 which provides a sterile gas permeable environment containing therein a sensor array 16.

SUMMARY OF THE INVENTION

The present invention relates to a cell culture chamber 10 having a sterile environment 12 for the culture of cells, a cover 14 for allowing for a transfer of gases and a sensor array 16.

DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION

Figure 1:
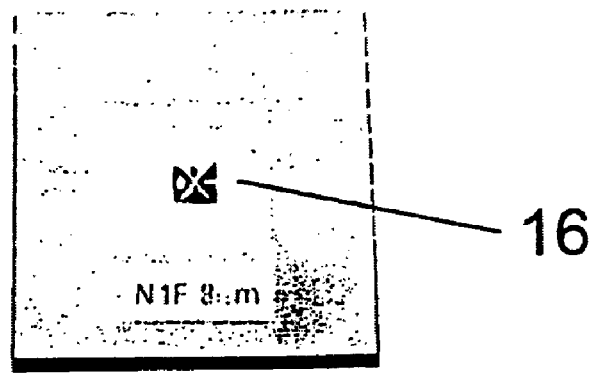
FIG. 1 is a photograph showing the sensor array 16 chip bonded with the ceramic 100-pin pin grid array (near actual size)
Figure 2:
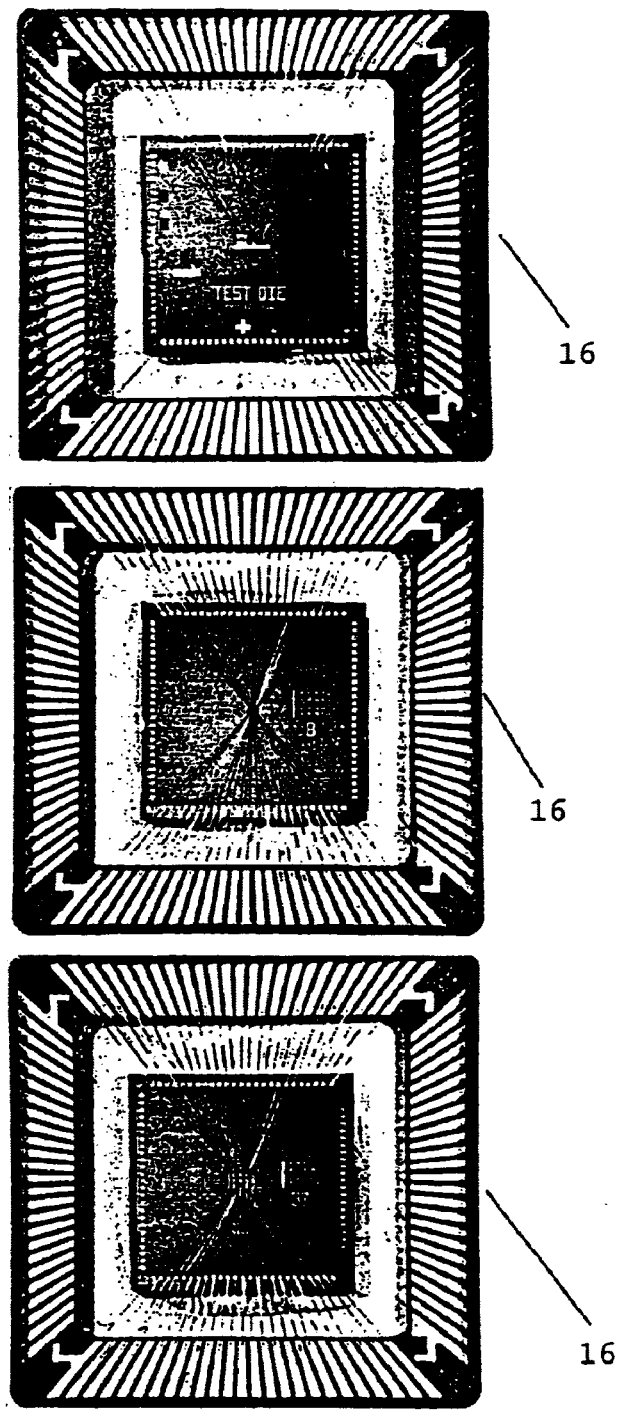
FIGS. 2A–C are photomicrographs of the sensor array 16 chip wire-bonded to the ceramic carriers' insert, Figure A is the test sensor, Figure B is an 8 μm electrode sensor array 16, and Figure C is a 32 μm electrode sensor array 16.

Generally, the present invention provides a cell culture chamber 10 providing a sterile environment 12 for the culture of cells, a cover 14 for allowing the free transfer of gases, and a sensor array 16.

By "sterile environment 12" it is meant that the environment or area in which the cells are being grown is devoid of contaminants and bacteria. The definition of contaminants differs depending upon the cells being cultured, and the specific property being measured. For example, the chamber 10 can include a Petri dish or other container. Any such sterile environment 12 must have a hole drilled in the bottom of sufficient size to accommodate the sensor array 16.

By "cover 14" it is meant a device sufficient to maintain the sterility of the environment while enabling the free transfer of required gases. These gases will differ depending upon the cells being cultured and the property being measured. In the preferred embodiment, the cover 14 is made of a clear material which enables a user to observe the culture medium, sensor, and cells. However, the cover 14 can also include a semi-permeable membrane. This membrane can be made of a hydrophobic or hydrophilic material.

The present invention permits detection and monitoring of membrane, chemical, and electrical characteristics of a cell. As noted at the outset, these characteristics include cell impedance (cell membrane capacitance and conductance), action potential parameters, cell membrane capacitance, cell membrane conductance, neuronal action potential, cellular metabolic products (hormones, neurotransmitters, waste products, etc.), and cell/substrate seal resistance. These electrical characteristics, in turn, correlate well with the metabolic state of the cell. The present invention, thus, provides an apparatus and method for monitoring cells and for monitoring the impact that an analyte has upon the metabolism of a cell. It is to be appreciated that such analytes include pharmaceutical agents, drugs, environmental factors, toxins, chemical agents, biological agents, viruses, and cellular adhesion promoters. Poly-D-lysine and Matrigel matrix (Becton Dickinson Labware, Bedford, Mass.) were used to provide a basement membrane for the cells.

The sensor array was first coated with poly-Dlysine to promote bonding of the Matrigel matrix. Sterile poly-D-lysine, at a concentration of 10 μg/ml in distilled water, was applied to each of the 2 mm×2 mm exposed sensor arrays and allowed to incubate at room temperature for 2 hours. The poly-D-lysine solution was then aspirated with a sterile pipette. The sensor arrays were placed at an incline with lids off in a sterile laminar flow hood and allowed to dry for 1.5 hours.

Matrigel matrix was thawed overnight in a refrigerator, and then diluted to 1:40 in cold DMEM/F12 (Life Technologies, Rockville, Md.). 20 μl of the Matrigel matrix was applied to each sensor array and spread evenly using a Pasture pipette. The solution was allowed to completely dry at room temperature in a sterile laminar flow hood. The Matrigel application was then repeated.

The sensor arrays could be stored for at least 2 months with one coat of poly-D-lysine and one coat of Matrigel matrix. The final coat of Matrigel matrix must be applied on the day of use. Under the microscope, a dry coated sensor appeared to have a fine, frost-like mesh. Care was taken to avoid opaque clots indicating the Matrigel matrix concentration was too high.

Thus, the present invention is useful in screening and assaying broad classes of materials for their impact on cellular metabolism.

Figure 8:
FIG. 8 is a photomicrograph at hNT neurons growing on the sensor array.

Cells are cultured within the medium according to known techniques. A layer of cells (FIG. 8) adhere to the respective surfaces of the microelectrode array provided on the integrated device. As each of the microelectrodes is driven with the applied voltage signal a current flows between the microelectrodes and the reference electrode. The impedance is determined from this current signal. Based on the impedance, various electrical characteristics of the cells which adhere to the surfaces of the microelectrodes can be monitored. Such characteristics include the impedance of the individual cell (i.e., the combined cell membrane capacitance and conductance), the action potential parameters of the individual cell, the cell membrane capacitance, the cell membrane conductance, and the cell/substrate seal resistance. The electrodes can also monitor the membrane potential produced by the cell, such as neuronal action potentials. The action potential parameters include, among others, action potential rate, action potential amplitude, and action potential shape and action potential power spectrum.

It is a feature of the invention that each of the microelectrodes is sufficiently small to enable monitoring of an individual cell, and its cellular membrane, and any secreted cellular products or metabolites. Conventionally, the relative size of the reference electrode is large in comparison to the measuring electrodes so that the measured impedance across each electrode and the reference electrode is dominated by the interface between the microelectrode and the cell and the cell membrane impedance. In addition, the present invention utilizes microelectrodes with a small surface such that the diameter of a cell is larger than the diameter of a microelectrode so that electrical and chemical characteristics related to individual cells and cell membranes can be resolved.

The specific size of the microelectrodes varies according to the specific application and size of the cells to be monitored Preferably, the diameter of the microelectrodes is less than or equal to one-half the diameter of the cell to be monitored, thereby permitting a given microelectrode to monitor an individual cell and cell membrane. For example, in one preferred embodiment, microelectrodes with diameters of about 4 to 20 $\mu$m have been utilized. The combination of the relatively small size of the microelectrodes, the relatively: low impedance of the microelectrodes (i.e., relative to cell membrane impedance) and the low noise characteristics of the signal detection components enables the present invention to monitor changes in the electrical and chemical characteristics of the cell, including changes in the capacitance and conductance of the cellular membrane. It also permits a variety of other techniques, described in greater detail below. These techniques include monitoring the action potential parameters of the cells; monitoring activation of voltage-gated ion channels; pharmaceutical screening and toxin detection; identifying particular cell/microelectrode junctions characterized by a higher degree of cell adherence to the microelectrode; and testing changes in cell adherence as adhesion promoting agents are employed.

It is understood that the signal monitoring and processing means referred to includes various devices for calculating the various cellular characteristics referred to above. For example, this element can comprise a personal computer configured to calculate the impedance between each microelectrode and the reference electrode based on the signals detected with the signal detecting means. By monitoring these values over time, the present invention can determine the various characteristics of individual cells which adhere to each microelectrode. The signal monitoring and processing means can be configured to perform a spectral analysis so as to monitor, in real time, characteristics such as changes in cell action potential parameters and cell impedance. The sensors can also be operated to perform amperometric and potentiometric determinations of chemical compositions and concentrations.

The surface of a single microelectrode of the array is exposed through a via in a passivation layer provided over a substrate. The microelectrode is driven with a signal source relative to the reference electrode.

The microelectrode has a known impedance Zero As known in the art, this value is described by a classical model of a metal in an electrolyte, and is calculated based on the material of the microelectrode or is measured separately prior to introduction of cells into the system. In series with the impedance of the microelectrode is the resistance of the solution $R_{soln}$ and the respective capacitance and conductive values associated with the microelectrode/cell junction. Parasitics to the substrate and parasitics to the passivation layer, can be reduced by use of a glass substrate, or can be factored out by normalizing.

Although often modeled as constants in prior art systems, the values of the capacitance and conductance associated with the cell actually vary in response to added toxins, pharmaceuticals and other substances, applied voltages, and changes in cellular morphology.

The impedances of the microelectrode, $Z_{elect}$, and the reference electrode, $Z_{ref}$, can be determined in a variety of ways. These values, as well as the resistance of the solution, $R_{soln}$, can be factored out, for example, by normalizing to data obtained prior to introduction of the cells to the system. Thus, by measuring the total impedance across each microelectrode and the reference electrode, it is possible to resolve impedances or changes in impedance relating to cell motility, adhesion to the cell substrate (based on $R_{seal}$), and changes in cellular membrane capacitance and conductance. It is further possible to monitor the activity of cellular ion channels and the action potential parameters of the cell as a result of their effects on the impedance measured between each microelectrode and the reference electrode or by actually monitoring the cell membrane potential.

It is noted that the particular electrical characteristics of the cell, such as the capacitance and the conductance of the cellular membrane, are determined from the measured impedance by modeling the cell in accordance with known techniques. Various cell models can be used. For example, the cell can be modeled as a flat, circular "pancake" (i.e., as a disk). Other models can include a square or rectangular "pancake", a sphere, a cube, or a rectangular box.

In an embodiment of the invention, a homodyne detection technique is used to detect the signals resulting from the application of a signal voltage between each microelectrode and the reference electrode. A quadrature synthesizer is used to generate both sine and cosine signals of a programmed frequency and amplitude. The sine voltage signal is attenuated as needed and selectively applied to individual microelectrodes. The resulting signal is detected by a transimpedance stage which holds the large reference electrode at a reference potential (in this case, ground) via negative feedback. Automatic gain control is used to amplify the voltage output of the transimpedance stage. The amplified signal is multiplied in quadrature by the source signals and is low pass filtered to provide the real and imaginary components of the measurement. Quadrature multiplication allows for signal detection, for example, at the excitation frequency with high noise immunity. Known resistance values are used to calibrate the system for electrode impedance measurements.

In another embodiment, a quadrature synthesizer generates both a sine wave and cosine wave, A sin (ωt) and A cos (ωt). In this particular example, the generated signals have a frequency of 1 kHz and an amplitude of 10 V peak to peak (P—P). Of course, it is understood that the present invention is not limited to these particular values. For example, a system has been constructed capable of applying signals from 100 Hz to 100 kHz.

The sine wave is attenuated in this example, in a range from 0 to −80 dB. The attenuated signal is then selectively applied to particular microelectrodes. In this example, an analog multiplexer is used to apply the attenuated voltage signal to each of an array of fifty-eight microelectrodes. Again, the invention is not limited to the number of microelectrodes in the array or to the components used for selective application of the signal to each of the microelectrodes.

The resulting current is detected by a transimpedance amplifier which maintains the large reference electrode at a virtual ground potential. The transimpedance amplifier outputs a signal, B sin ((ω+φ). In this example, a known resistance $R_{sense}$, is applied across the input and output of the transimpedance amplifier.

The signal from the transimpedance amplifier is then amplified by an automatic gain control (AGC) amplifier having a variable gain $A_V$. The signal is amplified in a range between 0 and 120 dB. The resulting signal, $A_V$ B sin (G)ωφ), is multiplied in quadrature with mixers 38a and 38b and then low pass filtered to obtain real and imaginary components X and Y.

Thus, the signal from AGC amplifier is mixed with the signal A sin ((ω.t) to obtain the following signal:

$(A_V AB/2)[\cos\phi\cos(2\omega t+\phi)]$

The signal from the AGC amplifier is also mixed with the signal A cos (ωt) to obtain the following signal:

$(A_V AB/2)[\sin++\sin(2\omega t+\phi)]$

Thus, when low pass filtered, the following components remain:

$X=(A_V AB \cos\phi)/2$ and $Y=(A_V AB \sin+)/2$

In one example, the system is calibrated with a known value resistance to obtain calibration values $X_{CAL}$ and $Y_{CAL}$. The magnitude $|CAL|$ and phase $\phi_{CAL}$ of the calibration values are then determined as follows: $\phi_{CAL}=\arctan[Y_{CAL}/X_{CAL}]|CAL|=[X_{CAL}^2+Y_{CAL}^2]^{1/2}$ Once the calibration values are obtained, measurements are taken with the microelectrodes and measurement values $X_{MEAS}$ and $Y_{MEAS}$ are calculated as indicated above. Based on these values, the phase and magnitude for the respective measurements, $\phi_{MEAS}$ and $|MEAS|$ are calculated as follow:

$\phi_{MEAS}=\arctan[X_{MEAS}/Y_{MEAS}]|MEAS|=[X_{MEAS}^2+Y_{MEAS}^2]_{1/2}$

Given the respective values for $X_{CAL}$, $Y_{CAL}$, $X_{MEAS}$ and $Y_{MEAS}$ one can divide the magnitude of the measured value $|MEAS|$ by the magnitude of the calibration value $|CAL|$ and then solve for the magnitude of the unknown impedance $|Z_{UNKNOWN}|$. The phase of the unknown impedance $Z_{UNKNOWN}$ is determined as follows:

The detected values for X and Y are sampled with an analog to digital (A/D) converter installed in a PC. In this example, a signal monitoring and processing means, such as a PC, receives the detected signal through an (A/D) converter at a sample rate sufficient to read the detected sinusoidal signal. For example, the output from the AGC amplifier could be A/D converted and input to a PC. The signal monitoring and processing means obtains phase and magnitude values from the unknown impedance after directly converting the respective sinusoidal output for extraction of data. In this example, the signal monitoring and processing means provides the capability of performing a spectral analysis to monitor, in real time, characteristics such as changes in cell action potential parameters and cell impedance. By performing real time Fourier analysis, it is possible to monitor distortion caused by nonlinear electrode effects. Thus, it is a feature of the invention that the system can perform spectral analysis of the resulting signals in order to monitor changes in various characteristics in real time.

As described generally above, data obtained with the embodiment can be "normalized" to various conditions in order to monitor the characteristics of cells which adhere to the respective microelectrodes. For example, the membrane capacitance and conductance of individual cells which adhere to the microelectrodes can be monitored, based on various models of the cells. Various other techniques are described herein.

This embodiment provides high sensitivity and signal resolution for a large range of applications. One characteristic of this embodiment is that the low pass filters have a characteristic settling time. Where several electrodes are monitored sequentially, this characteristic can introduce a minor delay. It is possible to provide an even faster measurement cycle by heterodyning the detected signal to a higher frequency and then bandpass filtering to obtain phase and magnitude information. Such a technique permits real time observation of extremely rapid variations in electrical characteristics of the cell, such as variations in transmembrane impedance (caused by opening and closing of ion channels).

A test signal oscillator generates sine and cosine signals, A sin ($\omega_{test}$ t) and A cos ($\omega_{test}$ t) at a frequency $\omega_{test}$. The voltage sine signal is selectively applied across each microelectrode and the reference electrode. The resulting current is detected using transimpedance amplifier and AGC amplifier. Mixers multiply the resulting signal B sin ($\omega_{test}t+\phi$) in quadrature by sine and cosine signals generated by a local oscillator. The signals produced by the local oscillator have an angular frequency $\omega_{LO}$, which is the sum of the test frequency $\omega_{test}$ and an intermediate frequency $\omega_{IF}$. As indicated above, the respective outputs of mixers are represented, respectively, by:

$(AB/2)\cos[(\omega_{IF}t+\phi]-(AB/2)\cos[(2\omega_{test}+\omega_{IF})t+\phi](AB/2)\sin[\omega_{IF}t+\phi]-(AB/2)\sin[(2\omega_{test}+\omega_{IF})t+\phi]$ These outputs are bandpass filtered at the intermediate frequency $\omega_{IF}$ and the filtered output detected using amplitude modulation detectors to provide real and imaginary components $X=|(AB \cos\phi)/2|$ and $Y=|(AB \sin\phi)/2|$. The algebraic sign of X and Y must be determined by a phase-sensitive detector, as is well known in the art. The unknown impedance between the microelectrode and the large reference electrode is then calculated in the manner described above.

It is appreciated that in addition to the exemplary embodiments discussed above, various other alternative embodiments are possible for impedance measurement. For example, measurement in the time domain can be used rather than homodyning to extract phase and magnitude information about each impedance. This can be accomplished, for example, by using a step function in place of the above-mentioned sinusoidal signal to drive each microelectrode. Further, the frequency of excitation and the sinusoidal input signal amplitude can be expanded beyond the exemplary ranges identified above.

Again, various modifications and alternative embodiments will be apparent to those skilled in the art without departing from the invention. For example, the microelectrodes and their respective interconnects and bond pads may comprise any biocompatible conductive substance, such as iridium, activated iridium, gold, platinum, polysilicon, aluminum, ITO, or TiW, bare or electroplated with platinum black.

Additionally, the substrate of the integrated device may be composed of a variety of materials, such as silicon, glass, metal, quartz, plastic, ceramic, polyethylene, or any other suitable type of polymer. It is noted that glass substrates have been found to provide reduced parasitic capacitance.

Other variations of the structure which are not essential to the underlying features of the invention include changes in the composition of the passivation layer. For example, devices made in accordance with the invention have utilized different passivation layers ranging from 0.5 to 5 $\mu$m in thickness. The passivation layer may comprise any suitable material, including low stress PECVD silicon nitride, silicon carbide, TEFLON™, polyimide, ceramic, photoresist, or any type of polymer or thermal plastic, or combination thereof.

Cloning cylinders, housed in Petri dishes, are bonded to the substrate to define respective wells. The Petri dishes can comprise polystyrene, glass, polyethylene, TEFLON™, metal, or any other type of polymer. The Petri dishes may be bound to a chip formed in accordance with the invention using conventional materials and techniques, such as epoxy, polyurethane, wax, or thermoplastic, using chemical, thermal, or ultrasonic processes. In this alternate construction, bondwire connections can be eliminated by use of a substrate configured to mate directly with a connector, such as an edge card connector or pads for a standard pin type connector. Of course, this would require the substrate area to be significantly larger than the active electrode area.

The membrane capacitance, membrane conductance, cell-substrate separation and action potential parameters of a cell are significant markers regarding a cell's metabolic state, including general cellular health and ionic channel activity. The membrane potential, the voltage difference across a cell's plasma membrane, depends on the distribution of ionic charge. Generally, the distribution of ionic charge determines the electric potential, or voltage. For example, in a metallic conductor, the mobile particles carrying charge are electrons; in an aqueous solution, the mobile particles are ions such as $Na^-$, $K^+$, $Cl^-$, and $Ca^+2$. In an aqueous solution, the number of positive and negative charges are normally balanced exactly, so that the net charge per unit volume is zero. An unbalanced excess of positive charges creates a region of high electrical potential, repelling other positive charges and attracting negative charges. An excess of negative charges repels other negative charges and attracts positive charge. When an accumulation of positive charges on one side of a membrane is balanced by an equal and opposite accumulation of negative charges on the other side of the membrane, a difference of electrical potential is set up between the two sides of the membrane.

Selective molecular access to the electrodes can be provided by depositing membranes on therm. Several different classes of membranes are available for use. Nafion acts as a cation exchange membrane (Brazell, et al., 1987), allowing only uncharged molecules to gain access to the electrodes. Additionally, various mixtures of cellulose acetate can be prepared which act as size exclusion membranes, allowing only specific molecular weight species to gain access to the electrodes. This is critical when monitoring large bioagent molecules. Often, large bioagent molecules degrade into a variety of break-down products. It is possible that only the parent bioagent exerts a biological effect and the break down products do not, however, several of the break down products may oxidize at potentials very close to the parent molecule when monitored amperometrically. Using a variety of decreasing size exclusion membranes on the sensors in the array, the concentration of the parent bioagent molecule can be determined as well as each of its breakdown products uniquely.

Charge is carried back and forth across the cell membrane by small inorganic ions—chiefly $Na^+$, $K^+$, $Cl^-$, and $Ca^+2$-but these can traverse the lipid bilayer only by passing through special ion channels. When the ion channels open, the charge distribution shifts and the membrane potential changes. Of these ion channels, those whose permeability is regulated are the most significant; these are referred to as gated channels. Two classes of gated channels are of crucial importance: (1) voltagegated channels, especially voltage-gated $Na^+$ channels, which play the key role in the rapid changes in electrical energy by which an action potential is propagated along a nerve cell process; and (2) ligand-gated channels, which convert extracellular chemical signals into electrical signals, which play a central role in the operation of synapses. These two types of channels are not particular to neurons: they are also found in many other types of cells.

One goal of the present invention is to augment semiconductor sensor technologies with new formulations of membranes containing ionophores, antibodies and enzymes, to enable the array to monitor a wide range of biological analytes, environmental toxins, as well as standard blood chemistries (i.e. electrolytes, antibodies, steroid and protein hormones, anesthetics, a variety of herbicides, medicinal drugs, drugs of abuse, etc.). One example of monitoring complex molecules with a membrane is to catalize or inhibit a reaction such as the measurement of the pesticide Paraoxon. Other complex molecules, such as neurotoxins and molecules of biological warfare can be detected by immobilizing antibodies and/or enzymes on the surface of an ion-selective membrane, by performing Enzyme Linked Immuno Sorbent Assays (ELISA), or through the production of amperometrically detectable reaction products catalyzed by enzymes causing the formation of electroactive molecules, such as hydrogen peroxide, from the parent molecule.

Because organophosphates inhibit the reaction mechanism causing the breakdown of various choline compounds, catalyzed by a variety of cholinesterase enzymes, these can be used to monitor the presence of Paraoxon. The membranes must adhere well to the silicon surface to prevent detachment of the membrane during sampling, rinsing, and washing of sensors in the sampling chamber. When silicon based, optical detectors are to be utilized, slight pealing of the membrane can significantly alter the performance of the device. Membranes that adhere strongly to the silicon surface provide the sensors with a long, useful, lifetime.

Some examples of membranes include, but are not limited to, Cellulose Acetate, Poly-Urethane/Poly-Vinyl Chloride, and Silicone Rubber. Each of these membrane compositions possess differing properties as related to enzyme and antibody immobilization and adherence to the silicon nitride surface of microscopic solid-state chemical sensors. Several methods are available for immobilizing enzymes and antibodies on the surface of the membranes.

Additional techniques amenable to monitoring organophosphorous containing compounds, including Paraoxon, can also be used. Sensitive assays using spectrofluorimetry have been reported to have detection limits on the order of $8 \times 10^{-7}$ for Paraoxon (Russell et al., 1999). Enzymes have been incorporated into a hydrophilic polyurethane membrane and deposited on top of hydrophobic polyurethane membranes (Cho et al., 1999), promoting adhesion to the sensor surface. Additionally, enzymes can be immobilized on the membrane surface that cause local changes in pH in the presence of toxins, which can be monitored utilizing a potentiometric electrode (Mutchandani et al., 1999) The first method to be employed for the detection of organophosphorus compounds such as Paraoxon is to monitor the inhibition of the reaction catalyzed by butyrylcholinesterase, which breaks down butyrylcholine into choline and butyric acid. Paraoxon has been shown to inhibit this reaction linearly in proportion to its concentration (Campanella, et al., 1996).

Membrane adhesion has typically been a significant problem effecting useful lifetime of solid-state chemical sensors. Many of the membranes utilized for traditional chemical sensors do not adhere well to the silicon-nitride surface, reducing the yield and lifetime. Membrane adhesion is tested using a QTest II adhesion analyzer. Membrane adhesion is a critical factor and must be optimized to provide stable electrochemical properties in a flow system. The fluid flow system, necessary for sample delivery, calibration, washing, and regeneration of the sensors, tends to cause pealing of the membrane.

To improve membrane adhesion, treatments and modifications of the sensor's silicon-nitride surface are examined in order to improve membranelsilicon-nitride cross-linking. These efforts vastly extend the useful lifetime of commercial devices.

Membranes can be deposited using a set of micropipettes accurate to 20 nL of volume. Other methods known to those of skill in the art can also be used to deposit the membrane. For example, one device, a New Long LS-15TV screen printing system for patterning membranes and epoxies onto sensor surfaces can print with +/−5 micron alignment and 25 to 50 micron minimum feature size.

Other features of the invention will become apparent in the course of the following descriptions of exemplary embodiments which are given for illustration of the invention and are not intended to be limiting thereof.

EXAMPLE

A mammalian cell culture chamber 10, with an integrated silicon sensor array 16, was designed, constructed, and tested. The chamber 10 provides a sterile environment 12 for the culture of cells. The chamber 10 has a cover 14 that allows free transfer of metabolic gases, minimizes medium evaporation, and allows sterile transport of the cell culture between an incubator and test stations (microscope, experimental setup, laminar flow hood, etc.). The silicon sensor array 16 is a general purpose device which may be modified to detect and quantify a wide range of analytes depending upon the electronic method of operation at amperometric sensors and upon the selection of membrane ionophore for the potentiometric sensors.

Figure 5:
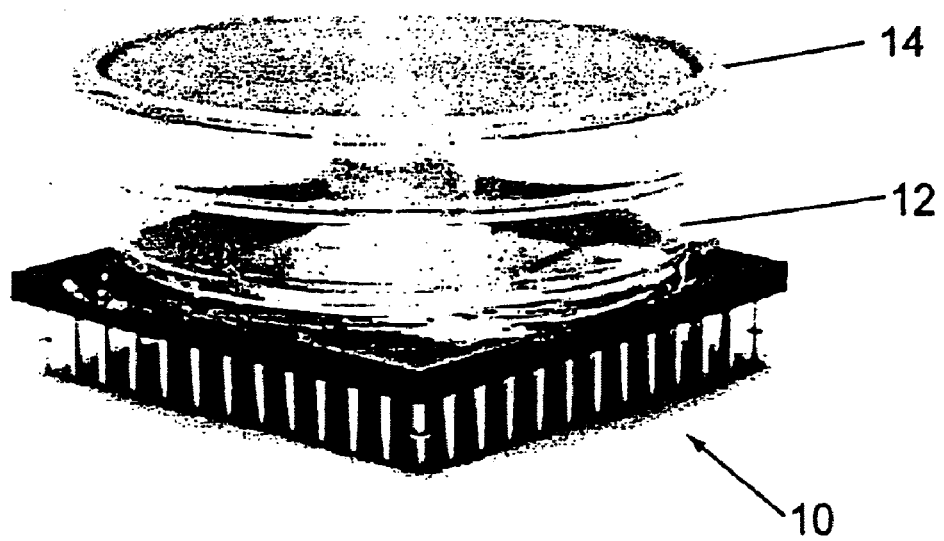
FIG. 5 is a side view of the preferred embodiment of the cell culture chamber of the present invention.
Figure 6:
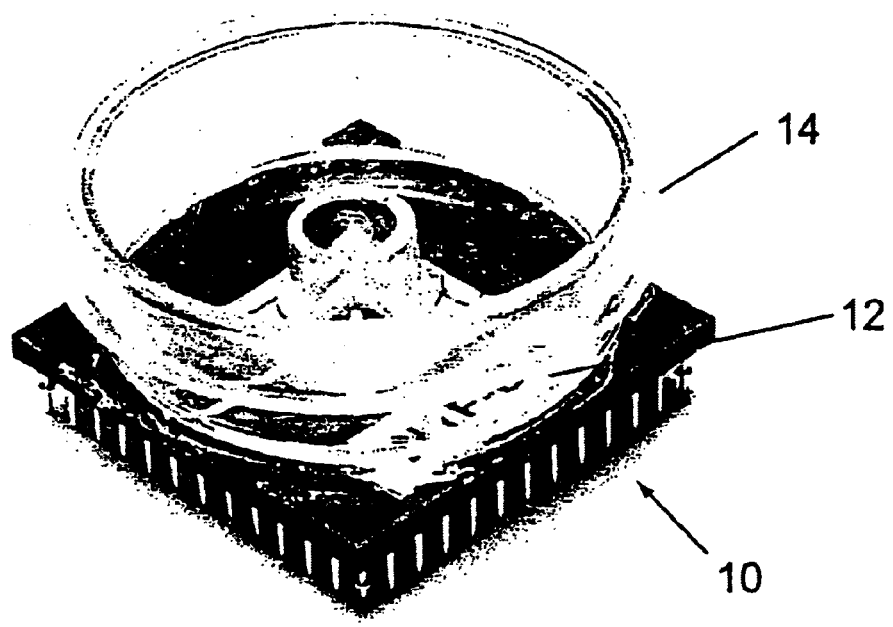
FIG. 6 is another view of the preferred embodiment of the cell culture chamber of the present invention.
Figure 7:
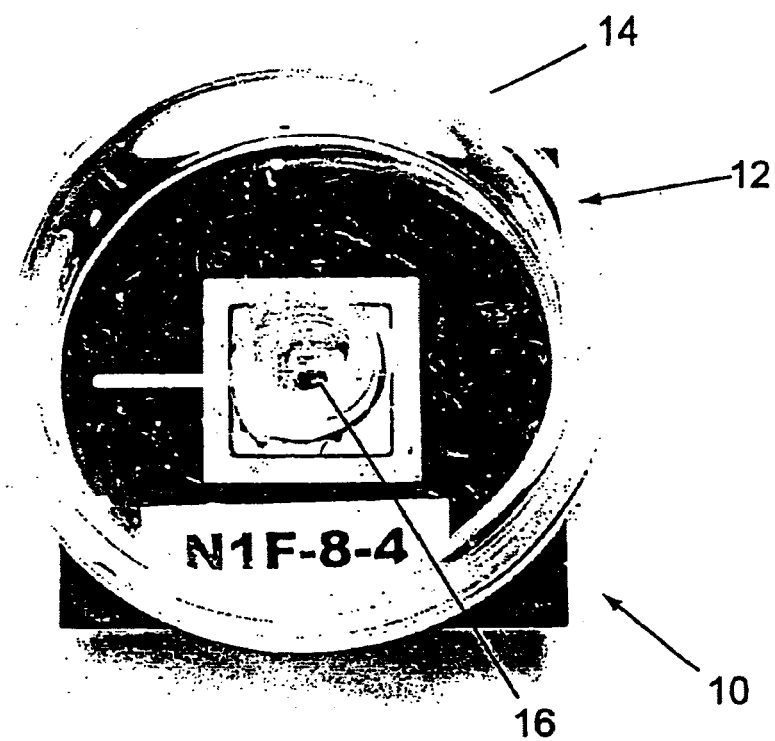
FIG. 7 is a top view of the preferred embodiment of the cell culture chamber of the present invention.

The sensor chips are packaged in a ceramic 100-pin pin grid array (PGA) package (Spectrum Semiconductor Materials, Inc., San Jose, Calif.) with gold plated pins and interconnects (FIGS. 1 and 5). The ceramic package body offers several advantages-when used in tissue culture. First, ceramic material is heat resistant allowing autoclave temperatures required for sterilization. Second, the thermal properties of ceramic material provide temperature stability when used for in vitro studies. During the short period when moving the chips from the incubator to an experimental station (i.e. microscope, laminar flow hood, electronic test station, etc.) the ceramic material acts as a thermal buffer minimizing temperature fluctuations at the cells.

Additionally, when forming the sensor array, the completed wirebonds are quite fragile and form an electrical connection to the growth media if exposed. Therefore, an epoxy material, Epoxy Patch 1C (Dexter Corporation), is used to seal the bonds. The bonded ceramic packages are heated to approximately 130° C. Epoxy Patch is carefully applied to the hot packages with the heat causing the material to liquefy and flow easily around the bonds to seal them. After curing at 130° C. for 30 minutes the result is a hard, durable coating that provides excellent electrical isolation and completely resists moisture exposure.

Figure 3:
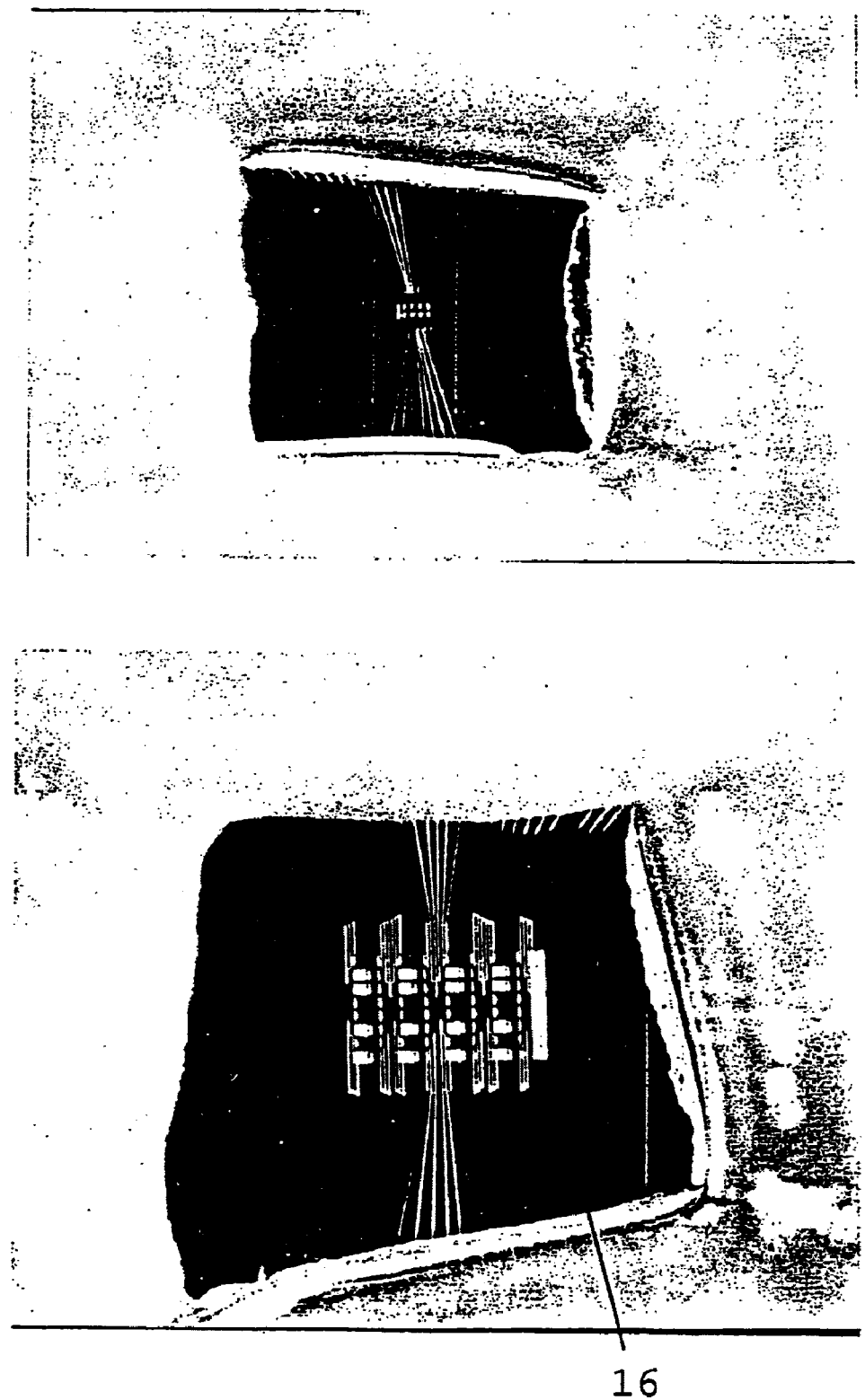
FIGS. 3A and B are pictures showing the silicone applied to the top of the sensor chip leaving approximately 2 mm×2 mm exposed over the sensor array 16, Figure A shows a 2 μm electrode sensor array 16, and Figure B shows an 8 μm electrode sensor array 16.
Figure 4:
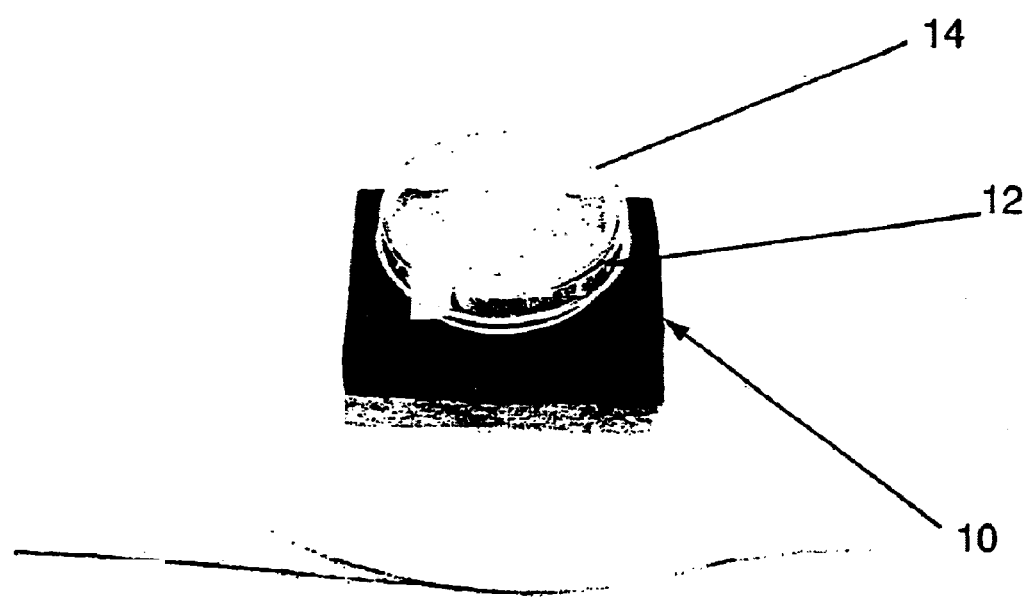
FIG. 4 is a picture showing the image of the entire cell culture chamber 10 with the integrated sensor array 16, cells and medium are maintained in the cloning cylinder mounted on top of the sensor array 16 in the 35 mm. Petri dish which maintains sterility during transport and minimizes fluid evaporation.

Once the sensor array 16 is secured within the ceramic carrier, a layer of inert Dow Corning Silicone RTV Sealant 732 (World Precision Instruments, Inc. Sarasota, Fla.) or any similar inert silicone or other sealant is applied leaving a 2 mm×2 mm window over the actual sensor array 16 (FIG. 3). A small, sterile cloning cylinder (Fisher Scientific, Chicago, Ill.) is placed over this window and attached with silicone. Finally, a 35 mm Petri dish (Fisher Scientific, Chicago, Ill.), with a hole drilled in the bottom to accommodate the cloning cylinder, is attached with silicone (FIG. 4). This arrangement provides several features:

1) the Petri is clear allowing observation of the culture medium, sensors, and cells;
2) the ability to transport the cells (cultured within the carrier chip) from an incubator to experimental station without compromising sterility; and 3) free transport of metabolic gases ($CO_2$, $O_2$) and, at the same time, minimal evaporation of the culture medium while housed in an incubator.

Figure 9:
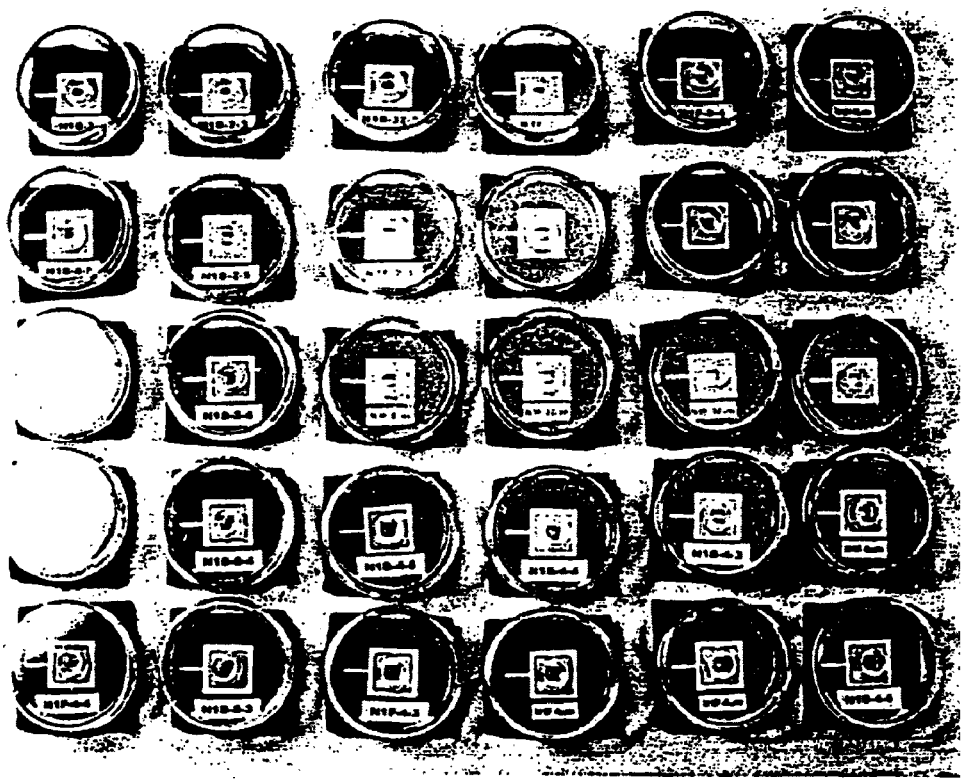
FIG. 9 is a picture of dozens of mammalian cell culture chambers.

Dozens of cell culture chambers 10 with integrated silicon sensor arrays 16 were constructed and tested in vitro (FIG. 9). Cultures of mammalian cells were maintained for periods greater than 75 days without a single incidence of contamination. The chambers 10 allowed free exchange of metabolic gases while minimizing medium evaporation as designed. The chambers 10 are designed such that it is technically simple to: 1) inoculate with cells; 2) transport between incubator and experimental station without compromising sterility; and 3) observe under a microscope.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

REFERENCES

Brazell, M. P. Feng, J., Kasser, R. J., Renner, K. J., and Adams, R. N., An improved method for Nafion coating carbon fiber electrodes for in vivo electrochemistry, *J. Neurosci. Meth.,* 22:167–172, 1987;

Campanella, L., Colapicchioni, G., Favero, G., Sammartino, M. P., Tomassetti, M., "Organophosphorus pesticide (Paraoxon) analysis using solid state sensors," Sensors and Actuators B 33(1996 25–33);

Cho, Y. A., Lee, H. S., Cha, G. S., Lee, Y. T., "Farbrication of butyrylcholinesterase sensor using polyurethane-based ion-selective membranes," Biosens Bioelectron 1999 Apr. 30;14(4):435–9

Ghosh, P. M. et al., "Monitoring Electropermeabilization in the Plasma Membrane of Adherent Mammalian Cells," Biophys. Journal, 64, 1602–09 (1993);

Giaever, I. et al., "Use of Electric Fields to Monitor the Dynamical Aspect of Cell Behavior in Tissue Culture," IEEE Transactions on Biomedical Engineering, Vol. BME-33, No. 2, February 1986;

Keese, (C. R. et al., "A Whole Cell Biosensor Based on Cell-Substrate Interactions," Annual International Conference of the IEEE Engineering in Medicine and Biology Society, Vol. 12, No. 2, (1990);

Keese, C. R., et al., "A Biosensor that Monitors Cell Morphology with Electrical Fields," IEEE Engineering in Medicine and Biology, June/July 1994, 402–08;

Kowolenko, M. et al., "Measurement of Macrophage Adherence and Spreading with Weak Electric Fields," Journal of Immunological Methods, 127, 71–77 (1990);

Lind et al., "Single Cell Mobility and Adhesion Monitoring Using Extracellular Electrodes" Biosensors and Bioelectronics, 6, 359–67 (1991);

Mulchandani, P., Mulchandani, A., Kaneva, I., Chen, W., "Bionsensor for direct determination of organophosphate nerve agents. 1. Potentiometric enzyme electrode," Biosens Bioelectron 1999 January 1; 14(1):77–85

Russell, R. J., Pishko, M. V., Simonian, A. L., Wild, J. R., "Poly(ehtylene glycol) hydrogelencapsulated fluorophore-enzyme conjugates for direct detection of organophosphorus neurotoxins," Analytical Chemistry 1999 November 1;71(21).4909–12

United States Patents

U.S. Pat. No. 4,054,646
U.S. Pat. No. 4,920,047
U.S. Pat. NO. 5,187,096

What is claimed is:

1. A cell culture chamber comprising:

a portable housing for maintaining a sterile environment for culture of cells therein, said housing including an opening therethough for access to a sensor array and an outer channel disposed about said opening and separated therefrom for containing a reactant therein for effecting the sterile environment; and a sensor array sealed within said opening and isolate from said outer channel.

2. The cell culture chamber according the claim 1, wherein said array is a silicon sensor array.

3. The cell culture chamber according the claim 2, wherein said sensor array is packaged in a ceramic pin grid array.

4. The cell culture chamber according the claim 1, wherein said chamber is a size small enough to be viewed under a microscope.

5. The cell culture chamber according to claim 1, wherein said sensor array is covered by a moisture resistant layer.

* * * * *